United States Patent [19]

Hirsch

[11] 4,170,702

[45] * Oct. 9, 1979

[54] PROCESS FOR POLYMERIZING A THIOBISPHENOL

[75] Inventor: Richard H. Hirsch, St. Louis, Mo.

[73] Assignee: Monsanto Company, St. Louis, Mo.

[ * ] Notice: The portion of the term of this patent subsequent to Jun. 27, 1995, has been disclaimed.

[21] Appl. No.: 918,737

[22] Filed: Jun. 23, 1978

Related U.S. Application Data

[63] Continuation-in-part of Ser. No. 751,774, Dec. 16, 1976, Pat. No. 4,097,534.

[51] Int. Cl.$^2$ .................. C07C 148/00; C07C 148/04
[52] U.S. Cl. ........................... 528/219; 260/45.95 C; 260/609 F
[58] Field of Search .................. 528/219; 260/609 F

[56] References Cited

U.S. PATENT DOCUMENTS

| 3,133,899 | 5/1964 | Kwiatek et al. | 260/47 |
| 3,306,874 | 2/1967 | Hay | 260/47 |
| 3,306,875 | 2/1967 | Hay | 260/47 |
| 3,707,565 | 12/1972 | Hofer | 260/45.95 X |
| 3,749,693 | 7/1973 | Cooper | 260/47 |
| 3,986,981 | 10/1976 | Lyons | 260/47 X |
| 4,097,534 | 6/1978 | Hirsch | 260/609 F |

Primary Examiner—Howard E. Schain
Attorney, Agent, or Firm—George R. Beck; Edward P. Grattan

[57] ABSTRACT

Low molecular weight polymers of 4,4'-thiobis(6-t-butyl-m-cresol) are prepared by contact with molecular oxygen in the presence of a copper salt complexed with amine. The polymer is useful as an antioxidant, e.g. for polyolefins.

25 Claims, No Drawings

PROCESS FOR POLYMERIZING A THIOBISPHENOL

CROSS-REFERENCE TO RELATED APPLICATION

This is a continuation-in-part of application Ser. No. 751,774 filed Dec. 16, 1976, and issuing June 27, 1978, as U.S. Pat. No. 4,097,534.

BACKGROUND OF THE INVENTION 4,4'-thiobis(6-t-butyl-m-cresol) (hereinafter also identified as TBC) is a highly effective antioxidant for various polymers, especially polyolefins. Under most conditions, TBC confers satisfactorily long-term oxidation resistance to polyolefins, and it has been recently found that under some conditions, certain polymeric forms of TBC provide even longer-term oxidation resistance for polyolefins. See U.S. Pat. Nos. 3,986,981 issued Oct. 19, 1976 to B. J. Lyons.

It has heretofore been known to polymerize other thiobisphenols with elimination of the sulfur link to product polyphenylene ethers which, in general, do not have the antioxidant effectiveness of the thiobisphenol monomer. For instance, U.S. Pat. No. 3,133,899 issued May 19, 1964 to J. Kwiatek et al. discloses preparation of polyaryl ethers by oxidative coupling of 2,6-disubstituted thiobisphenols accomplished by contacting the monomer with a free oxygen-containing gas in an organic solvent such a pyridine, and in the presence of a copper chloride catalyst. During the reaction, the sulfur is eliminated from the monomer and a sulfur-free, linear polyphenylene ether is obtained.

U.S. Pat. Nos. 3,306,874 and 3,306,875 issued Feb. 28, 1967 to A. Hay disclose preparation of polyphenylene ethers by polymerization of 2,6-disubstituted phenols in the presence of oxygen and a copper salt/amine complex catalyst. The reaction occurs between the dehydrogenated oxygen atom of one phenol and the dehydrogenated para-situated carbon atom of a second phenol to form the polyether product.

U.S. Pat. No. 3,749,693 issued July 31, 1973 to G. Cooper also discloses preparation of polyphenylene ethers by oxidizing 2,6-disubstituted phenols in the presence of a copper salt/amine complex catalyst.

As distinguished from the aforementioned process in which polymeric products are obtained from thiobisphenols with elimination of sulfur from the polymer chain, it is an object of this invention to provide a process by which TBC can be polymerized without the elimination of its sulfur atom, e.g. to provide polymers such as those described in U.S. Pat. No. 3,986,981. Another object is to provide such a process which proceeds relatively rapidly and with an attractive yield of the polymeric product. Other objects will be apparent from the following disclosure.

SUMMARY OF THE INVENTION

This invention provides a process for preparing a polymer represented by the formula

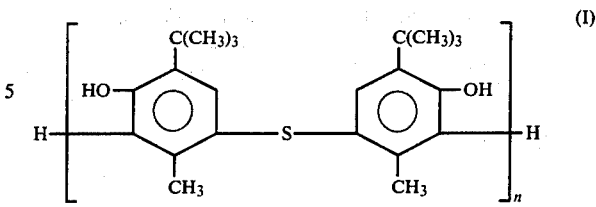

wherein n has a value from 2 to about 10 which comprises reacting 4,4'-thiobis(6-t-butyl-m-cresol) with molecular oxygen at a molar ratio from 2 to about 4 in the presence of a copper salt complexed with amine at a temperature from about 20° C. to the decomposition temperature of said polymer, the molar ratio of said cresol to said amine being less than about 50 and the molar ratio of said salt to said amine being less than about 1.4, said amine being selected from pyridine, cyclo($C_3$–$C_{12}$ alkyl)amines, $C_1$–$C_{20}$ alkylamines, di($C_1$–$C_{20}$ alkyl)amines, $C_2$–$C_{12}$ alkylene diamines and di- and tetra($C_1$–$C_2$ alkyl)-($C_2$–$C_4$ alkylene)diamines.

DETAILED DESCRIPTION OF THE INVENTION

Certain embodiments of the invention can be carried out by use of the process claimed in the afore-mentioned application Ser. No. 751,774. Other advantageous embodiments, e.g. as claimed herein, include those similar to those claimed in Ser. No. 751,744 but in which the molar ratio of the cresol to amine in the reaction mixture is less than about 40, the molar ratio of copper salt to amine in the reaction mixture is less than about 0.8, the copper salt is sulfate, the reaction temperature is from about 80° C. to the decomposition temperature of said polymer, the process is carried out in the presence of an amount of non-interfering dessicant sufficient to substantially accelerate the reacting of the cresol and/or the amine is selected from methylamine, ethylamine, n-propylamine, n-($C_5$–$C_{20}$ alkyl)amines, iso($C_3$–$C_{20}$ alkyl)amines, t-($C_5$–$C_7$ alkyl)amines, t-($C_9$–$C_{20}$ alkyl)amines, dimethylamine, dipropylamines, diisobutylamine, di-t-butylamine, di($C_5$–$C_{20}$ alkyl)amines, $C_2$–$C_{12}$ alkylene diamines such as hexamethylene diamine, di($C_1$–$C_2$ alkyl)-($C_2$–$C_4$ alkylene)diamines, tetraethyl-($C_2$–$C_4$ alkylene)diamines and tetramethyl-($C_3$–$C_4$ alkylene)diamines.

In accordance with the invention, it has been found that TBC can be polymerized to a polymer containing sulfur linkages between phenolic rings or, expressed otherwise, that the sulfur linkage between TBC phenolic rings is retained on polymerization of TBC by the present invention. Although the scope of the invention is not to be limited in accordance with any theory of its mechanism, it can be hypothesized that the t-butyl substituent on each phenolic ring in TBC hinders reaction by the oxygen atom ring substituent adjacent thereto and/or that the methyl substituent on each such ring hinders attack at the para-situated ring carbon atom to which the sulfur atom in TBC is bonded. Both of such reactions are necessary to form polyaryl ethers in the manner disclosed in U.S. Pat. No. 3,133,899, and are prevented in preparation of the sulfur-containing polymers produced by the process of this invention. Thus it may be seen that under the conditions of the process disclosed herein, importantly different results occur when the cresol is a 2,5-disubstituted thiobisphenol such as TBC rather than a 2,6-disubstituted thiobisphenol as employed in U.S. Pat. No. 3,133,899.

In preferred embodiments of the present process in which TBC is reacted with molecular oxygen in the presence of copper salt complexed with amine, the molar ratio of TBC to amine in the reaction mixture is less than about 50. In especially preferred embodiments, including many in which the amine is a diamine, and particularly a di- or tetra($C_1$–$C_2$ alkyl)-($C_2$–$C_4$ alkylene)diamine, that molar ratio is less than about 40, preferably from about 10 to about 40 and even more desirably from about 20 to about 40, although in most embodiments that ratio can be satisfactorily much lower (i.e., as low as about 0.1 or even lower), e.g. when the amine is also used as a reaction solvent or diluent.

As aforesaid, the process of this invention can be satisfactorily carried out using an amine selected from methylamine, ethylamine, n-propylamine, n-($C_5$–$C_{20}$ alkyl)amines, iso-($C_3$–$C_{20}$ alkyl)amines, t-($C_5$–$C_7$ alkyl)amines, t-($C_9$–$C_{20}$ alkyl)amines, dimethylamine, dipropylamines, diisobutylamine, di-t-butylamine, di($C_5$–$C_{20}$ alkyl)amines, $C_2$–$C_{12}$ alkylene diamines such as hexamethylene diamine, di($C_1$–$C_2$ alkyl)-($C_2$–$C_4$ alkylene)diamines, tetraethyl-($C_2$–$C_4$ alkylene)diamines and tetramethyl-($C_3$–$C_4$ alkylene)diamines. Of those amines, the diamines are generally preferred, and especially good results can be obtained with use of di($C_1$–$C_2$ alkyl)-($C_2$–$C_4$ alkylene)diamines, tetraethyl-($C_2$–$C_4$ alkylene)diamines and tetramethyl-($C_3$–$C_4$ alkylene)diamines. In general, even more superior results are obtainable with use of di- or tetra($C_1$–$C_2$ alkyl)-($C_2$–$C_3$ alkylene)diamines. Typically, monoamines must be used in amounts substantially greater than such diamines.

Also as aforesaid, the invention may be advantageously carried out in the presence of an amount of non-interfering dessicant sufficient to substantially accelerate the reacting of said cresol. Such a dessicant can be, for example, magnesium sulfate, calcium sulfate, any of a variety of molecular sieves or other essentially neutral substances capable of functioning as a dessicant in the reaction medium while being non-interfering with the intended reaction, i.e., not interfering to prevent substantial formation of the desired polymeric product. Such dessicants have been found particularly useful in accelerating the reaction carried out in the presence of copper salt complexed with a di-($C_1$–$C_2$ alkyl)-($C_2$–$C_4$ alkylene)diamine. Generally, magnesium sulfate is preferred for use as such a dessicant.

The reaction can be carried out in the presence of essentially any copper salt which can be complexed with a suitable amine. Typically the salt is selected from chloride, bromide, acetate, propionate, butyrate, palmitate, benzoate and sulfate. Of those salts, the chloride is normally most preferred. Addition of the salt in its cuprous form is generally preferred, although satisfactory results are obtainable in many cases with addition of the cupric form of the salt.

Also as aforesaid, the invention can be carried out using a reaction mixture in which the molar ratio of copper salt to amine is less than about 1.4. Although in many embodiments that ratio is at least about 0.8, it may be satisfactorily lower in many other embodiments. In such other embodiments, that ratio is usually at least about 0.6, although it may be substantially lower (i.e., as low as about 0.01 or even lower), e.g. when the amine is also used as a reaction solvent or diluent.

Also as aforesaid, the invention may be carried out at a temperature from about 20° C. to the decomposition temperature of the polymeric product, which is normally about 250° C. In general, minimum product coloration occurs when the reaction is carried out at a temperature no higher than about 80° C., and it is expected that no intolerable additional product color would result at reaction temperatures from about 80° C. up to about 110° C. or, in some cases, substantially higher. Normally, however, a reaction temperature from about 45° to about 60° C. is optimum.

The process of this invention is desirably carried out in a diluent for the TBC and copper salt/amine catalyst complex. Diluents which may be satisfactorily used include, for example, benzene, toluene, xylene, substituted benzenes such as chlorobenzene and nitrobenzene, esters such as butyl acetate, and various amines including an excess of the amine used to provide the salt/amine complex which catalyzes the polymerization reaction. Preferably the diluent serves as a solvent for the salt/amine complex but, although such solvating properties are important, the main purpose of the diluent is to provide a liquid phase in which the TBC and catalyst complex may properly interface.

As used herein, the term "molecular oxygen" means oxygen not chemically combined with other elements. It is typically provided to the reaction mixture in an oxygen-containing gas which may be pure molecular oxygen or molecular oxygen mixed with at least one other gas, e.g. air. Pure gaseous oxygen is preferred for ease of calculating and controlling molar ratios for the reaction.

The catalyst complex may be preformed or formed in situ. For example, preformed catalyst can be prepared by combining the copper salt, amine and diluent and heating the resulting mixture to the temperature desired for TBC polymerization. Thereafter, TBC is charged to the mixture and the flow of molecular oxygen into the mixture is initiated. Alternatively, the TBC, amine and diluent can be combined and then heated to the desired polymerization temperature, after which the copper salt is charged and the flow of molecular oxygen is begun. It is generally preferred to use preformed catalyst which typically affords higher reaction rates.

Products of the present process are normally polymers specifically represented by Formula I hereinbefore, although in some embodiments there may be produced a substantial proportion (typically lower than about 25% by weight) of essentially similar polymers additionally comprising at least one end-group or internal unit consisting of a fragment (usually approximately one half) of a TBC molecule. Such process embodiments, to the extent that they provide polymeric product nevertheless containing two or more of the sulfur-linked units represented in Formula I, should be considered equivalents of the process embodiments disclosed and claimed herein.

Except for the presence of such additional TBC fragments, the molecular weight of the product of this process is essentially directly proportional to the amount of oxygen which reacts with the TBC, and a polymer of approximately predetermined chain length may thus be obtained by use of a calculated ratio of moles of TBC and oxygen, which is taken up quantitatively in the reaction.

To illustrate further with respect to the products specifically represented by Formula I, "n" has the following relationship to the moles of TBC and oxygen which react:

$$n = \frac{1}{1-2\left(\frac{\text{moles } O_2}{\text{moles TBC}}\right)}$$

Thus to obtain such a polymeric product in which n is from 2 to about 10, TBC is reacted with oxygen at a molar ratio from about 2.2 to about 4 moles of TBC per mole of oxygen. In typical uses of the polymer as a polyolefin antioxidant, the average number of repeating units (n) is advantageously from about 2.7 to about 5; such polymers are obtained by reacting TBC with oxygen at a molar ratio from about 2.5 to about 3.2. Frequently even more desirably, the polymeric product has from about 2.7 to about 4 repeating units and is produced by reacting TBC with oxygen at a molar ratio from about 2.7 to about 3.2. Molecular weight of polymeric product is essentially 356.5 times the number of such repeating units.

The following specific examples of the process of this invention are illustrative only and do not imply any limitations on the scope of the invention.

EXAMPLE 1

Cuprous chloride (0.1 g; 1.0 mmole) and tetramethylethylene diamine (0.1 g; 0.9 mmole) were stirred in 100 g. toluene in an atmosphere of pure oxygen. After 30 minutes at about 25° C., TBC (14.3 g; 0.04 mole) was added in one portion and the reaction vessel was put in open communication with a source of additional pure gaseous oxygen. When 330 ml. (0.015 mole) oxygen had reacted, 5% hydrochloric acid (50 ml.) was added. The mixture was then stirred for 30 minutes and the aqueous phase discarded. Temperature of the mixture had remained between 25° and 35° C. throughout the reaction. After a water (50 ml.) wash, the toluene phase was concentrated, yielding 13.5 g. of a light yellow solid having nuclear magnetic resonance (NMR) spectra consistent with those expected for the polymer represented by Formula I. By gel permeation chromatography (GPC) the product was found to have an average molecular weight of 1360 (average n of about 3.8).

EXAMPLE 2

Cresol/amine molar ratio=21

TBC (30.2 g; 0.084 mole), cuprous chloride (0.4 g; 4.0 mmole) and tetramethylethylene diamine (0.46 g; 4.0 mmole) were stirred in 262 g. benzene at about 50° C. Air was then bubbled through the mixture at about 4000 ml/hr. After 1 hr, 802 ml. oxygen had reacted as determined by measurement of the volume of gas exiting the reaction mixture. Temperature of the mixture remained between 48° and 55° C. throughout the reaction. Product work-up as described in Example 1 provided an essentially quantitative yield of a yellow solid having NMR spectra consistent with those expected for polymer of Formula I and an average molecular weight (by GPC) of about 1390.

EXAMPLE 3

Use of a dessicant and a dialkylalkylene diamine 3-dimethylaminopropylamine (0.102 g; 1.0 mmole) and cuprous chloride (0.1 g; 1.0 mmole) were stirred in 125 ml. toluene at 25° C. in an atmosphere of pure gaseous oxygen. After 1 hr anhydrous magnesium sulfate (6.3 g; 0.05 mole) was added, followed by TBC (14.3 g; 0.04 mole). The reaction vessel was then put in open communication with a reservoir of gaseous oxygen maintained at slightly over atmospheric pressure. After 23 minutes, 330 ml. (0.015 mole) oxygen had reacted and the temperature of the mixture had remained between 25° and 35° C. throughout the reaction. Product work-up as described in Example 1 provided a yellow solid having an average molecular weight of about 1300 (by GPC) and analytical data (infrared and NMR spectroscopy) consistent with those expected for polymer represented by Formula I.

EXAMPLE 4

Molar ratio of copper salt to amine=0.89

Cuprous chloride (0.1 g; 1.01 mmole) and tetramethylethylene diamine (0.132 g; 1.14 mmole) was stirred in 211 ml. benzene at about 23° C. while air was passed over the surface of the mixture. After 18 minutes, TBC (14.5 g; 0.0404 mole) was added. After 70 minutes, 256 ml. oxygen had reacted, as determined by measuring the volume of gas exiting the reaction mixture, and the temperature of the mixture had remained between 23° and 28° C. throughout the reaction. Work-up as described in Example 1 provided a yellow solid having an average molecular weight of about 915.(GPC) and NMR spectra consistent with those expected for polymer represented by Formula I. After mechanical losses in the work-up, product yield was 89.2%.

EXAMPLE 5

Molar ratio of copper to amine=0.46

Tetramethylethylene diamine (0.265 g; 2.28 mmole) and cuprous chloride (0.104 g; 1.05 mmole) were stirred in 81.2 g. toluene at about 50° C. in an atmosphere of pure gaseous oxygen. After 33 minutes, TBC (30.05 g; 0.084 mole) was added and the reaction vessel was then put in open communication with a reservoir of gaseous oxygen maintained at slightly over atmospheric pressure. After 97 minutes, 727 ml. oxygen had reacted and the temperature of the mixture had been maintained between 50° and 53° C. throughout the reaction. Work-up as described in Example 1 gave a 99.2% yield of a yellow solid having an average molecular weight of about 1260 (by NMR) and NMR spectra consistent with those expected for polymer represented by Formula I.

EXAMPLE 6

Cuprous chloride (0.205 g; 2.07 mmole) and tetramethylethylene diamine (0.24 g; 2.07 mmole) were stirred in 81.4 g. toluene at 23° C. in an atmosphere of pure gaseous oxygen. The mixture was heated to 43° C. over 0.5 hr, after which TBC (30.32 g; 0.0846 mole) was added and the reaction vessel was then put in open communication with a reservoir of pure gaseous oxygen maintained at slightly over atmospheric pressure. After 35 minutes, 730 ml. oxygen had reacted and the temperature of the mixture had remained between 43° and 47° C. throughout the reaction. Work-up as described in Example 1 gave a 96% yield of a yellow solid having an average molecular weight of about 960 (by NMR) and NMR spectra consistent with those expected for polymer represented by Formula I.

EXAMPLE 7

In another illustration of the process of this invention, 105.7 g (0.29 mole) of TBC is reacted with 3.45 g (0.11 mole) pure gaseous oxygen in the presence of 0.73 g (7.4 mmole) cuprous chloride and 0.73 g (6.3 mmole) tetramethylethylene diamine between 50° and 55° C. to afford 100 g (0.08 mole) of polymer having an average molecular weight of 1378 and a structure as shown in Formula I. In that illustration, the molar ratio of TBC to oxygen is 2.73 (weight ratio=30.6), the molar ratio of TBC to cuprous chloride is 39.98 (weight ratio=144.8), the molar ratio of TBC to amine is 46.93 (weight ratio=144.8) and the molar ratio of cuprous chloride to amine is 1.17 (weight ratio=1.0).

The foregoing examples and disclosure illustrate use of preferred embodiments of the process of this invention. Additional embodiments will be readily apparent to those skilled in the art. For example, similar results may be obtainable with the use of other copper salts, other amines (e.g. triamines, etc.) and/or molar ratios between reaction mixture constituents that are somewhat different from those specifically described herein, and in those instances such variations of the invention should be regarded as equivalents of those specifically disclosed and claimed herein.

I claim:

1. Process for preparing a polymer represented by the formula

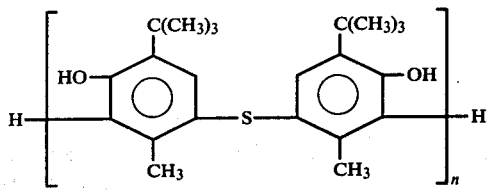

wherein n has a value from 2 to about 10 which comprises reacting 4,4'-thiobis(6-t-butyl-m-cresol) with molecular oxygen at a molar ratio from 2 to about 4 in the presence of copper salt complexed with amine at a temperature from about 20° C. to the decomposition temperature of said polymer, the molar ratio of said cresol to said amine being less than about 40 and the molar ratio of said salt to said amine being less than about 1.4, said amine being selected from pyridine, cyclo($C_3$–$C_{12}$ alkyl)amines, $C_1$–$C_{20}$ alkylamines, di($C_1$–$C_{20}$ alkyl)amines, $C_2$–$C_{12}$ alkylene diamines and di- and tetra($C_1$–$C_2$ alkyl)-($C_2$–$C_4$ alkylene)diamines.

2. Process of claim 1 wherein the salt is selected from chloride, bromide, acetate, propionate, butyrate, palmitate, benzoate and sulfate.

3. Process of claim 1 carried out in the presence of an amount of non-interfering dessicant sufficient to substantially accelerate the reacting of said cresol.

4. Process of claim 1 carried out in a diluent for said cresol at a temperature no higher than the boiling point of said diluent.

5. Process of claim 1 wherein said cresol is reacted with oxygen at a molar ratio of from about 2.5 to about 3.2.

6. Process of claim 1 wherein said temperature is not higher than about 110° C.

7. Process of claim 6 carried out in the presence of copper chloride complexed with di- or tetra($C_1$–$C_2$ alkyl)-($C_2$–$C_3$ alkylene)diamine, said molar ratio of cresol to amine being at least about 10 and said molar ratio of salt to amine being at least about 0.6.

8. Process of claim 7 wherein said amine is tetramethylethylene diamine.

9. Process for preparing a polymer represented by the formula

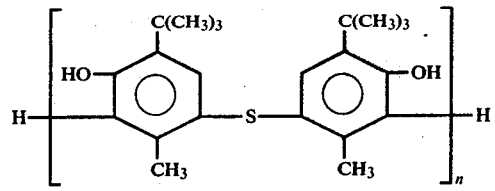

wherein n has a value from 2 to about 10 which comprises reacting 4,4'-thiobis(6-t-butyl-m-cresol) with molecular oxygen at a molar ratio from 2 to about 4 in the presence of copper salt complexed with amine at a temperature from about 20° C. to the decomposition temperature of said polymer, the molar ratio of said cresol to said amine being less than about 50 and the molar ratio of said salt to said amine being less than about 1.4, said amine being selected from methylamine, ethylamine, n-propylamine, n-($C_5$–$C_{20}$ alkyl)amines, iso($C_3$–$C_{20}$ alkyl)amines, t-($C_5$–$C_7$ alkyl)amines, t-($C_9$–$C_{20}$ alkyl)amines, dimethylamine, dipropylamines, diisobutylamine, di-t-butylamine, di($C_5$–$C_{20}$ alkyl)amines, $C_2$–$C_{12}$ alkylene diamines, di($C_1$–$C_2$ alkyl)-$C_2$–$C_4$ alkylenediamines, tetraethyl-($C_2$–$C_4$ alkylene)diamines and tetramethyl-($C_3$–$C_4$ alkylene)diamines.

10. Process of claim 9 wherein the salt is selected from chloride, bromide, acetate, propionate, butyrate, palmitate, benzoate and sulfate.

11. Process of claim 10 wherein said amine is diamine, said ratio of cresol to amine being at least about 10 and said ratio of salt to amine being at least about 0.6.

12. Process of claim 11 carried out in a diluent for said cresol in the presence of copper chloride at a temperature no higher than about 110° C.

13. Process of claim 12 carried out in the presence of an amount of non-interfering dessicant sufficient to substantially accelerate the reacting of said cresol.

14. Process for preparing a polymer represented by the formula

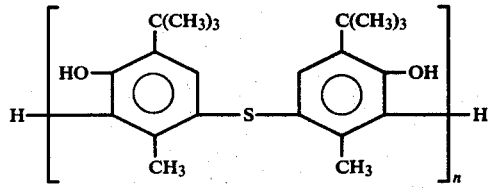

wherein n has a value from 2 to about 10 which comprises reacting 4,4'-thiobis(6-t-butyl-m-cresol) with molecular oxygen at a molar ratio from 2 to about 4 in the presence of copper salt complexed with amine at a temperature from about 20° C. to the decomposition temperature of said polymer, the molar ratio of said cresol to said amine being less than about 50 and the molar ratio of said salt to said amine being less than about 1.4, said process being carried out in the presence of an amount of non-interfering dessicant sufficient to substantially accelerate the reacting of said cresol and said amine being selected from pyridine, cyclo($C_3$-$C_{12}$ alkyl)amines, $C_1$-$C_{20}$ alkylamines, di($C_1$-$C_{20}$ alkyl)amines, $C_2$-$C_{12}$ alkylene diamines and di- and tetra($C_1$-$C_2$ alkyl)-($C_2$-$C_4$ alkylene)diamines.

15. Process of claim 14 wherein the salt is selected from chloride, bromide, acetate, propionate, butyrate, palmitate, benzoate and sulfate and said temperature is no higher than about 110° C.

16. Process of claim 15 carried out in a diluent for said cresol in the presence of copper chloride complexed with di- or tetra($C_1$-$C_2$ alkyl)-($C_2$-$C_4$ alkylene)diamine, said ratio of cresol to amine being at least about 10 and said ratio of salt to amine being at least about 0.6.

17. Process for preparing a polymer represented by the formula

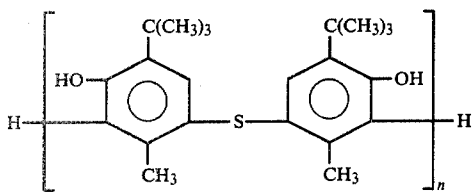

wherein
n has a value from 2 to about 10 which comprises reacting 4,4'-thiobis(6-t-butyl-m-cresol) with molecular oxygen at a molar ratio from 2 to about 4 in the presence of copper sulfate complexed with amine at a temperature from about 20° C. to the decomposition temperature of said polymer, the molar ratio of said cresol to said amine being less than about 50 and the molar ratio of said salt to said amine being less than about 1.4, said amine being selected from pyridine, cyclo($C_3$-$C_{12}$ alkyl)amines, $C_1$-$C_{20}$ alkylamines, di($C_1$-$C_{20}$ alkyl)amines, $C_2$-$C_{12}$ alkylene diamines and di- and tetra($C_1$-$C_2$ alkyl)-($C_2$-$C_4$ alkylene)diamines.

18. Process of claim 17 wherein said amine is di- or tetra($C_1$-$C_2$ alkyl)-($C_2$-$C_3$ alkylene)diamine, said ratio of cresol to amine is at least about 10 and said ratio of salt to amine is at least about 0.6.

19. Process of claim 18 carried out in a diluent for said cresol at a temperature no higher than about 110° C., said amine being tetramethylethylene diamine.

20. Process for preparing a polymer represented by the formula

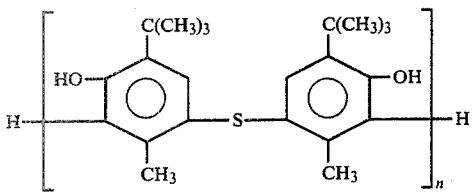

wherein n has a value from 2 to about 10 which comprises reacting 4,4'-thiobis(6-t-butyl-m-cresol) with molecular oxygen at a molar ratio from 2 to about 4 in the presence of copper salt complexed with amine at a temperature from about 20° C. to the decomposition temperature of said polymer, the molar ratio of said cresol to said base being less than about 50 and the molar ratio of said salt to amine being less than about 0.8, said amine being selected from pyridine, cyclo($C_3$-$C_{12}$ alkyl)amines, $C_1$-$C_{20}$ alkylamines, di($C_1$-$C_{20}$ alkyl)amines, $C_2$-$C_{12}$ alkylene diamines and di- and tetra($C_1$-$C_2$ alkyl)-($C_2$-$C_4$ alkylene)diamines.

21. Process of claim 20 wherein the salt is selected from chloride, bromide, acetate, propionate, butyrate, palmitate, benzoate and sulfate, said amine is selected from di- and tetra($C_1$-$C_2$ alkyl)-($C_2$-$C_3$ alkylene)diamines, said temperature is no higher than about 110° C., said ratio of cresol to amine is at least about 10 and said ratio of salt to amine is at least about 0.6.

22. Process of claim 21 carried out in a diluent for said cresol in the presence of copper chloride complexed with tetramethylethylene diamine.

23. Process for preparing a polymer represented by the formula

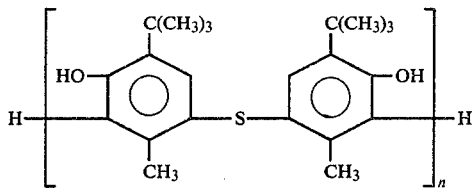

wherein n has a value from 2 to about 10 which comprises reacting 4,4'-thiobis(6-t-butyl-m-cresol) with molecular oxygen at a molar ratio from 2 to about 4 in the presence of a copper salt complexed with amine at a temperature from about 80° C. to the decomposition temperature of said polymer, the molar ratio of said cresol to said amine being less than about 50 and the molar ratio of said salt to said amine being less than about 1.4, said amine being selected from pyridine, cyclo($C_3$-$C_{12}$ alkyl)amines, $C_1$-$C_{20}$ alkylamines, di($C_1$-$C_{20}$ alkyl)amines, $C_2$-$C_{12}$ alkylene diamines and di- and tetra($C_1$-$C_2$ alkyl)-($C_2$-$C_4$ alkylene)diamines.

24. Process of claim 23 wherein the salt is selected from chloride, bromide, acetate, propionate, butyrate, palmitate, benzoate and sulfate, said amine is di- or tetra($C_1$-$C_2$ alkyl)-($C_2$-$C_3$ alkylene)diamine, said ratio of cresol to amine is at least about 10 and said ratio of salt to amine is at least about 0.6.

25. Process of claim 24 carried out in a diluent for said cresol in the presence of copper chloride complexed with tetramethylethylene diamine at a temperature no higher than about 110° C.

* * * * *

UNITED STATES PATENT AND TRADEMARK OFFICE
CERTIFICATE OF CORRECTION

PATENT NO. : 4,170,702

DATED : October 9, 1979

INVENTOR(S) : Richard H. Hirsch

It is certified that error appears in the above-identified patent and that said Letters Patent are hereby corrected as shown below:

Column 2, line 30, "Ser. No. 751,744" should read -- Ser. No. 751,774 --.

Column 5, line 17, "Molecular weight of poly-" should read -- Molecular weight of the poly- --.

Column 6, line 25, decimal point after "915" should be deleted.

Column 7, line 4, "molecular weight of 1378" should read -- molecular weight of 1328 --.

Signed and Sealed this

First Day of January 1980

[SEAL]

Attest:

SIDNEY A. DIAMOND

Attesting Officer

Commissioner of Patents and Trademarks